US006473509B2

(12) United States Patent
Albus et al.

(10) Patent No.: US 6,473,509 B2
(45) Date of Patent: Oct. 29, 2002

(54) AUDIO SYSTEM, IN PARTICULAR FOR MOTOR VEHICLES

(75) Inventors: Rainer Albus, Dormettingen (DE); Norbert Niemczyk, Pforzheim (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/862,999

(22) Filed: May 23, 2001

(65) Prior Publication Data

US 2002/0015502 A1 Feb. 7, 2002

(30) Foreign Application Priority Data

May 23, 2000 (DE) ........................................ 100 25 496

(51) Int. Cl.[7] .......................... A61F 11/06; H04R 3/00; H04B 1/00

(52) U.S. Cl. .......................... 381/71.4; 381/96; 381/86

(58) Field of Search .......................... 381/96, 71.4, 86

(56) References Cited

U.S. PATENT DOCUMENTS 4,712,247 A * 12/1987 Swarte ...................... 381/105
5,434,922 A 7/1995 Miller et al. ................. 381/57

FOREIGN PATENT DOCUMENTS

| | | |
|---|---|---|
| DE | 43 03 921 | 11/1994 |
| EP | 0 539 939 | 5/1993 |
| JP | 55003261 | 1/1980 |
| JP | 03235407 | 10/1991 |

* cited by examiner

*Primary Examiner*—Forester W. Isen
*Assistant Examiner*—Elizabeth McChesney
(74) *Attorney, Agent, or Firm*—Crowell & Moring LLP

(57) ABSTRACT

An audio system, in particular for motor vehicles, having a loudspeaker installation for supplying sound to an audio chamber and a control unit with a signal detection unit for receiving microphone signals from at least one microphone exposed to the audio chamber outputting the signal to an evaluation unit which extracts interference signals from the microphone signals. The control unit produces control signals on the basis of these interference signals in order to operate the loudspeaker installation. To reduce the complexity for installation of such an audio system, at least one tweeter is connected in the loudspeaker installation as a microphone.

15 Claims, 3 Drawing Sheets

AUDIO SYSTEM, IN PARTICULAR FOR MOTOR VEHICLES

BACKGROUND AND SUMMARY OF THE INVENTION

This application claims the priority of German Patent Document 100 25 496.9, filed May 23, 2000, the disclosure of which is expressly incorporated by reference herein.

The invention relates to an audio system, in particular for motor vehicles. Such an audio system is known, for example, from U.S. Pat. No. 5,434,922 which includes a loudspeaker installation for supplying sound to an audio chamber, e.g. a vehicle interior, and also a control unit which produces control signals for the purpose of operating the loudspeaker installation. In this case, this control unit is equipped with a correction device and has a signal detection unit which receives microphone signals from a microphone exposed to the audio chamber and forwards them to an evaluation unit which extracts interference signals from the microphone signals. The control unit then produces the control signals for operating the loudspeaker installation on the basis of these interference signals.

Such an audio system is used for intentionally supplying sound to an audio chamber in order to convey a particular acoustic impression to a listener situated in the chamber. To this end, the audio system contains at least one audio signal source, e.g. a radio, a CD player, a telephone installation, which provides audio signals on the basis of which the control signals for operating the loudspeaker installation are produced. The acoustic impression of the intentionally produced sound waves can be disrupted by noise, however. In a vehicle, the noise which disrupts the audio impression in the vehicle interior may be formed, by way of example, by noise from the tires on the ground, wind noise or noise created by an open window or an open sunroof. To be able to achieve the highest possible quality for the listener's acoustic impression, modern audio systems are equipped with a correction device which uses microphones to detect the sound in the audio chamber and extracts the noise or the interference signals correlating thereto from that sound. On the basis of the interference signals ascertained, the control in the audio system can then introduce suitable measures which reduce the influence of the noise on the acoustic impression for the listener and which improve the quality of the desired acoustic impression.

To be able to implement such an audio system in an audio chamber, e.g. in a vehicle interior, at least one microphone needs to be installed in the audio chamber in order to be able to detect the actual acoustic condition in the audio chamber permanently. The greater the number of arranged microphones, the more precise the actual acoustic condition in the audio chamber can be ascertained. However, installation of these additional microphones means an increased level of complexity when fitting such an audio installation.

EP 0 539 939 B1 discloses the practice of setting up the microphones in the vehicle interior in conjunction with one of the loudspeakers in the loudspeaker installation. In this way, microphone and loudspeaker form a standard assembly which can be fitted in the vehicle in unison. This allows the fitting complexity to be reduced.

The present invention is concerned with the problem of specifying, for an audio system of the type mentioned in the introduction, another way in which it is possible to reduce the fitting complexity for installation of the audio system.

The invention is based on the general concept of using or operating at least one tweeter in the loudspeaker installation as a microphone. In this context, the invention is based on the realization that, on the one hand, the noise which has a particularly intensive disruptive effect on the acoustic audio impression in a vehicle interior, in particular, is situated in a relatively low frequency range, whereas, on the other hand, the sound waves primarily radiated by a tweeter are situated in a relatively high frequency range. This means that a crossover frequency after which the tweeter is involved in the radiation of sound in the loudspeaker installation is situated above the frequency spectrum of the critical noise. On the basis of this realization, the invention proposes connecting the respective tweeter such that it operates as a loudspeaker above its crossover frequency and operates as a microphone below its crossover frequency. While relatively high-frequency electrical voltages entering in loudspeaker mode are converted into corresponding, relatively high-frequency sound waves and are radiated, relatively low-frequency sound waves arriving at the tweeter or at the diaphragm thereof prompt conversion, as a result of inductive processes, into corresponding, relatively low-frequency electrical voltages which can be picked off at the connections of the loudspeaker. These voltages form electrical interference signals correlating to the acoustic noise.

The advantages of such an embodiment are obvious, since no separate microphones need be provided, in which case the additional fitting of microphones is also dispensed with. The circuit or electronics required for producing the audio system according to the invention is less expensive than the microphones which it replaces and may be implemented during the actual manufacture of the audio system.

In accordance with one advantageous embodiment, the tweeter can be connected via a high-pass filter circuit to an output side of a loudspeaker amplifier whose input side receives the control signals from the control unit. As a result of this measure, no shorting is produced at the output of the loudspeaker amplifier during induction of the low-frequency microphone signals. By way of example, this high-pass filter circuit can be produced by passively decoupling the tweeter from the loudspeaker amplifier using a capacitor.

In accordance with one preferred development, the tweeter can be connected via a low-pass filter circuit to an input side of a microphone amplifier whose output side forwards the microphone signals to a signal detection unit. This embodiment ensures that the high-frequency control signals for the loudspeaker amplifier are not applied to the microphone amplifier.

To simplify the processing of the microphone signals and, in particular, to allow the processing to be carried out using a microprocessor, the signal detection unit preferably has an analog/digital converter which converts the incoming analog microphone signals into digital microphone signals and forwards them to a digital evaluation unit.

In accordance with one preferred embodiment, the control unit is able to control and/or regulate at least one of the following functions on the basis of the interference signals: equalizing, compression, limiter, level matching, filter matching. This allows, by way of example, dynamic equalizing to be achieved, where equalizing quality, equalizing gain and equalizing frequencies are influenced on the basis of the interference signals. Similarly, dynamic compression and a dynamic limiter function can be obtained, where, by way of example, a compression factor, a limiter threshold and the control times for attack and decay are accordingly set on the basis of the interference signals. In addition, dynamic level matching, i.e. interference-signal-dependent volume adjustment, and dynamic filter matching can be achieved, where, by way of example, the crossover frequencies, the gain factors and shape factors for bass filters, midrange filters and treble filters are set and readjusted on the basis of the interference signals.

Other objects, advantages and novel features of the present invention will become apparent from the following detailed description of the invention when considered in conjunction with the accompanying drawings.

A preferred exemplary embodiment of the invention is shown in the drawings and is explained in more detail in the description below.

BRIEF DESCRIPTION OF THE DRAWING

In the drawings, which are schematic in each case.

DETAILED DESCRIPTION OF THE PREFERRED EMBODIMENTS

Figure 1:
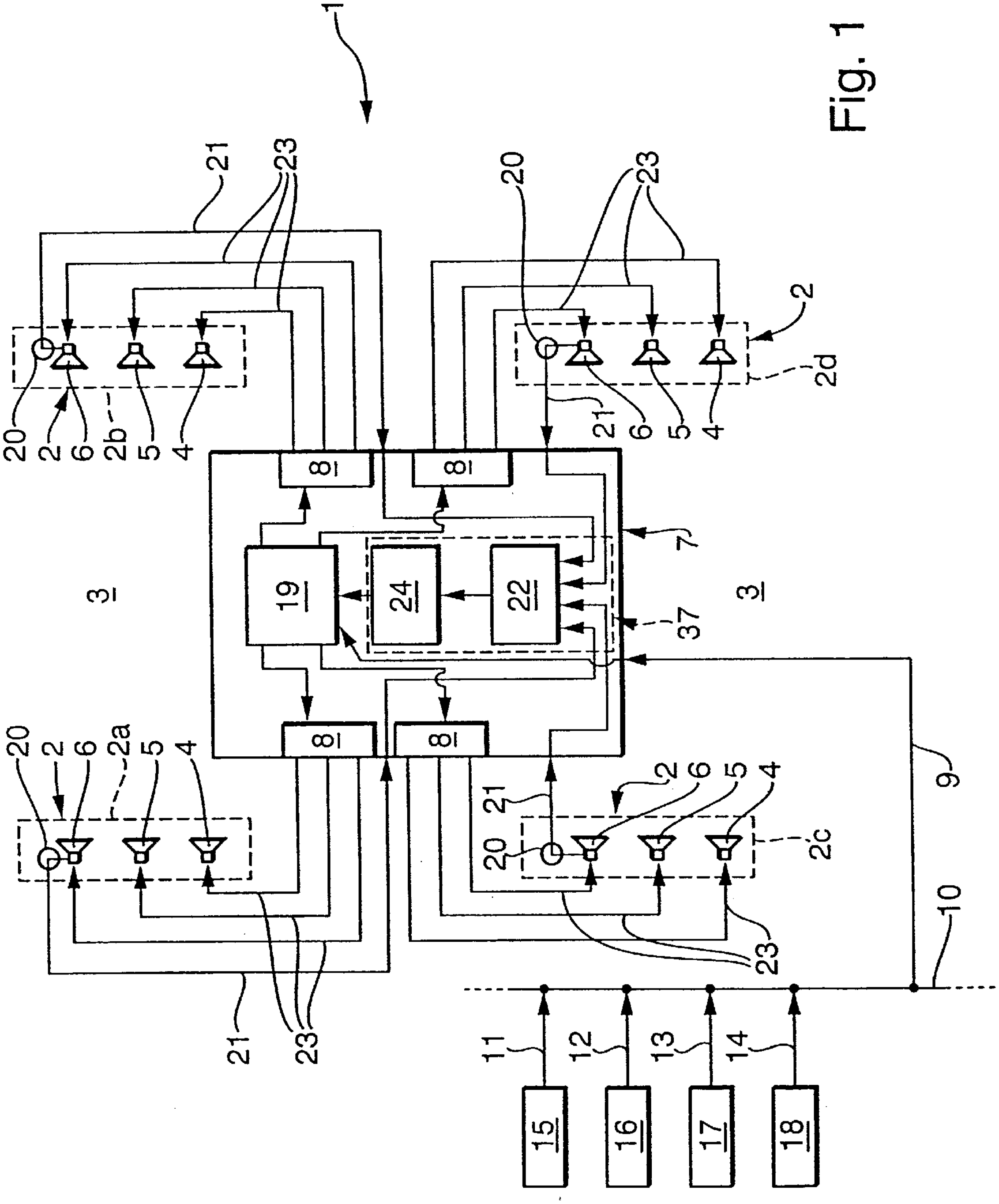
FIG. 1 shows a schematic basic illustration of a preferred embodiment of an audio system according to the invention.

In accordance with FIG. 1, an audio system 1 is equipped with a loudspeaker installation 2 which comprises four loudspeaker units 2*a*, 2*b*, 2*c*, 2*d* in the present exemplary embodiment. On the basis of one preferred use for this audio system 1, the individual loudspeaker units 2*a*, 2*b*, 2*c*, 2*d* in the loudspeaker installation 2 can be allocated to four physical areas of an audio chamber 3. When such an audio system 1 is fitted into a motor vehicle, the audio chamber 3 corresponds to the vehicle interior, and the loudspeaker unit 2*a* is situated on the front left-hand side, for example, while the loudspeaker unit 2*b* is arranged on the front right-hand side, the loudspeaker unit 2*c* is arranged on the rear left-hand side and the loudspeaker unit 2*d* is arranged on the rear right-hand side.

Each loudspeaker unit 2*a*, 2*b*, 2*c*, 2*d* has at least one woofer 4 for radiating low audio frequencies, at least one midrange unit 5 for radiating midrange audio frequencies and at least one tweeter 6 for radiating high audio frequencies. Naturally, the loudspeaker installation 2 may also have additional further loudspeakers.

The audio system 1 additionally has a control unit 7 which produces control signals for operating the loudspeaker installation 2. For this purpose, the control unit 7 can be equipped with appropriate loudspeaker amplifiers 8 which provide the control signals from the control unit 7 with the necessary signal strength for operating the individual loudspeakers 4, 5, 6 in the loudspeaker installation 2. The illustration chosen in this case is merely exemplary, which means that active loudspeakers with an integrated amplifier may likewise be used, which are operated directly using the control signals from the control unit 7. The loudspeaker amplifiers 8 operate the individual loudspeakers 4, 5, 6 in the loudspeaker installation 2 via appropriate cables 23.

Control unit 7 is connected to a data bus 10 by input line 9. The data bus 10 is connected by output lines 11, 12, 13 and 14 from audio components 15, 16, 17, 18 in the audio system 1. These audio components may, by way of example, be a radio 15, a CD player 16, a telephone installation with a hands-free facility 17 and a navigation installation with voice output 18. The aforementioned audio components 15 to 18 are each used as an audio signal source which transmits audio signals to the data bus 10 and makes them available to the control unit 7. The control unit 7 effects signal processing in order to produce suitable control signals for the loudspeaker installation 2. A data or signal processing unit in the control unit 7 is symbolized in FIG. 1 by a square marked by 19, with the square containing or being formed by a microprocessor, for example.

According to the invention, the tweeters 6 in the loudspeaker installation 2 are each connected as a microphone, with each tweeter 6 having an associated microphone amplifier 20. Since the microphone signals produced inductively in the tweeter 6 are relatively weak, it is expedient to arrange the microphone amplifiers 20 for amplifying the microphone signals close to the tweeters 6 or to integrate them therein. This means that the generated microphone signals can be amplified, practically at the place of origin, to such an extent that they can be transported further with relatively low susceptibility to interference until they are processed. Appropriate signal lines 21 are used to supply the amplified microphone signals to a signal detection unit 22.

The signal detection unit 22 forwards the microphone signals to an evaluation unit 24 in which interference signals correlating to the noise in the audio chamber 3 are extracted from the microphone signals. Since the tweeters 6 are optimally positioned for radiating sound in the audio chamber 3, their positioning is automatically also particularly well suited to the microphone function.

The evaluation unit 24 then forwards the extracted interference signals to the data processing unit 19, which then generates the suitable control signals from the audio signals on the basis of the interference signals and forwards them to the loudspeaker amplifiers 8.

On the basis of the interference signals, the control unit 7 or the data processing unit or microprocessor 19 thereof is able to control or regulate correction functions in order to improve the acoustic impression for a listener in the audio chamber 3. By way of example, dynamic equalizing, dynamic compression, a dynamic limiter function, dynamic level matching and/or dynamic filter matching are/is carried out on the basis of the interference signals. Other measures are likewise conceivable, such as the production of counteracting sound to reduce the noise in the audio chamber 3.

The signal detection unit 22 and the evaluation unit 24 coupled thereto form a correction device 37 which is implemented in the control unit 7. Naturally, the correction device 37 can be integrated using appropriate hardware elements and/or appropriate software components. In the present case, however, the correction device 37 cannot be clearly delimited, since the ascertained interference signals are processed in the data processing unit 19 in order to generate the control signals for operating the loudspeaker installation 2 on the basis of these interference signals. Accordingly, the actual correction does not take place until in the data processing unit.

Figure 2:
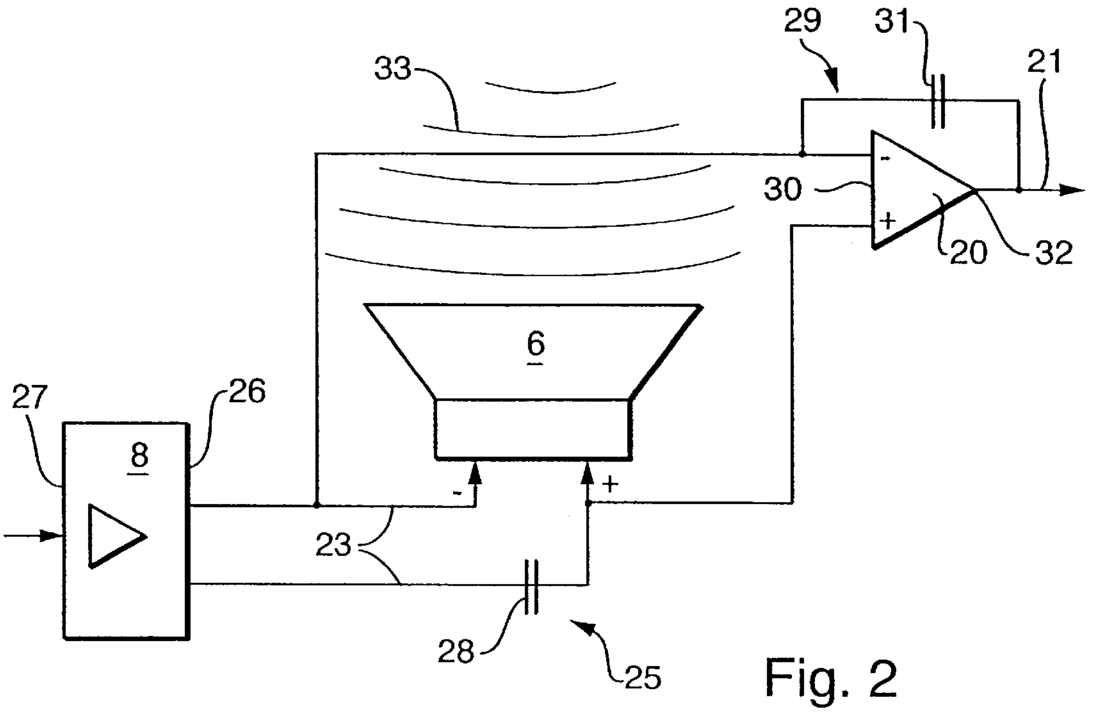
FIG. 2 shows a schematic circuit arrangement for producing a microphone function in a treble loudspeaker.

In accordance with FIG. 2, the tweeter 6 is connected to an output side 26 of the loudspeaker amplifier 8 via a high-pass filter circuit 25. As already shown in FIG. 1, an input side 27 of the loudspeaker amplifier 8 is supplied with the control signals from the control unit 7. In this case, the high-pass filter circuit 25 is produced by a capacitor 28 which passively decouples the tweeter 6 from the loudspeaker amplifier 8.

In addition, the tweeter 6 is connected to an input side 30 of the microphone amplifier 20 via a low-pass filter circuit 29. In this case, the low-pass filter circuit 29 is produced using an appropriate capacitor 31. An output side 32 of the microphone amplifier 20 is connected to the signal detection unit 22 by means of the signal line 21 (cf. FIG. 1).

The loudspeaker amplifier 8 is expediently designed to have a low impedance, whereas the microphone amplifier 20 is designed to have a high impedance.

For the loudspeaker mode of the tweeter 6, the loudspeaker amplifier 8 sends relatively high-frequency control signals to the tweeter 6. The high-pass filter circuit 25 serves to ensure that only a predetermined, relatively high frequency range reaches the tweeter 6 and is converted therein into sound waves. Simultaneously with its loudspeaker activity, the tweeter 6 can also operate as a microphone. In this context, low-frequency sound waves emanating from the noise and indicated by wave lines 33 in FIG. 2 stimulate corresponding oscillations in the diaphragm of the tweeter 6. Since there is a relatively large frequency difference between the high-frequency oscillations radiated by the tweeter 6 and the low-frequency oscillations of the noise which impinge thereon, the high-frequency oscillations and the low-frequency oscillations can be superimposed at the diaphragm in essence without detrimental interaction. The oscillations produced by the noise on the diaphragm of the tweeter 6 induce corresponding low-frequency voltages in the tweeter 6 which reach the microphone amplifier 30. As a result of the low-pass filter circuit 29, the microphone amplifier 20 amplifies only the low-frequency voltages and forwards them to the signal detection unit 22. In this context, the high-pass filter circuit 25 simultaneously prevents the low-frequency induced voltages from shorting the relevant output of the loudspeaker amplifier 8.

Figure 3:
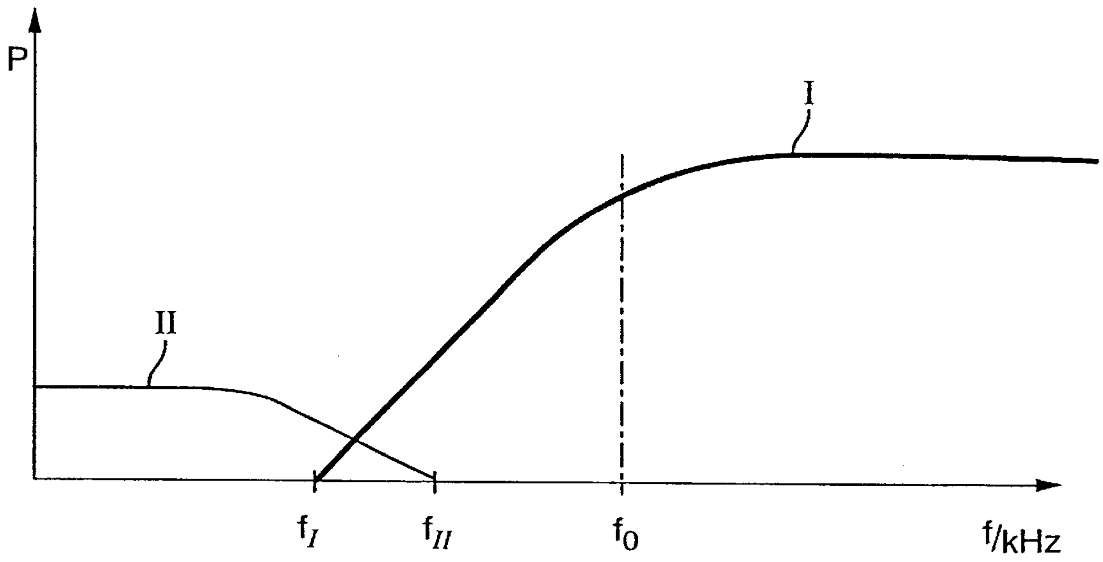
FIG. 3 shows a graph to illustrate a level curve as a function of frequency in a treble loudspeaker.

In the graph shown in FIG. 3, the frequency f is plotted on the abscissa while the level P is shown on the ordinate. This graph then shows, firstly, the level curve, as a function of frequency, on the tweeter during loudspeaker operation I thereof, and, secondly, the level curve on the tweeter during microphone operation II thereof. $f_0$ denotes a crossover frequency above which the tweeter is involved in the radiation of sound into the audio chamber. This crossover frequency $f_0$ is defined by the high-pass filter circuit and, in one preferred embodiment, may be adjusted by the control device 7. It is evident from FIG. 3 that the physical design of the tweeter means that it can be used to radiate sound waves only from a frequency $f_I$ upward. Similarly, it becomes clear that the physical design of the tweeter likewise means that it may be used as a microphone only up to a frequency $f_{II}$. These limits $f_I$ and $f_{II}$ are stipulated by the physical properties of the tweeter, in particular by the properties of the diaphragm and of the diaphragm drive. An appropriate choice of crossover frequency $f_0$ prevents reciprocal influencing of loudspeaker mode and microphone mode for the tweeter, which means that the tweeter can operate as a loudspeaker and as a microphone simultaneously. The operation of the tweeter as a microphone only up to a frequency $f_{II}$ is not a problem in the application provided here, since the critical noise occurs in a low-frequency range which is regularly situated below the crossover frequency $f_0$ and, in particular, also below the cutoff frequency $f_{II}$.

Figure 4:
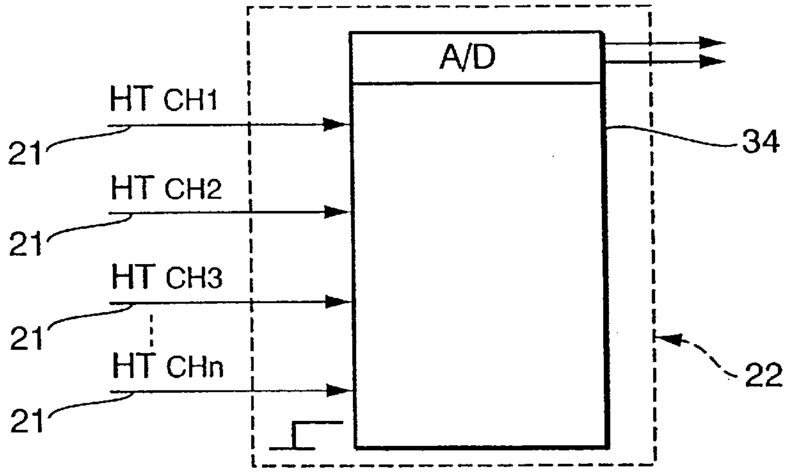
FIG. 4 shows a basic illustration of a first embodiment of a signal detection unit.
Figure 5:
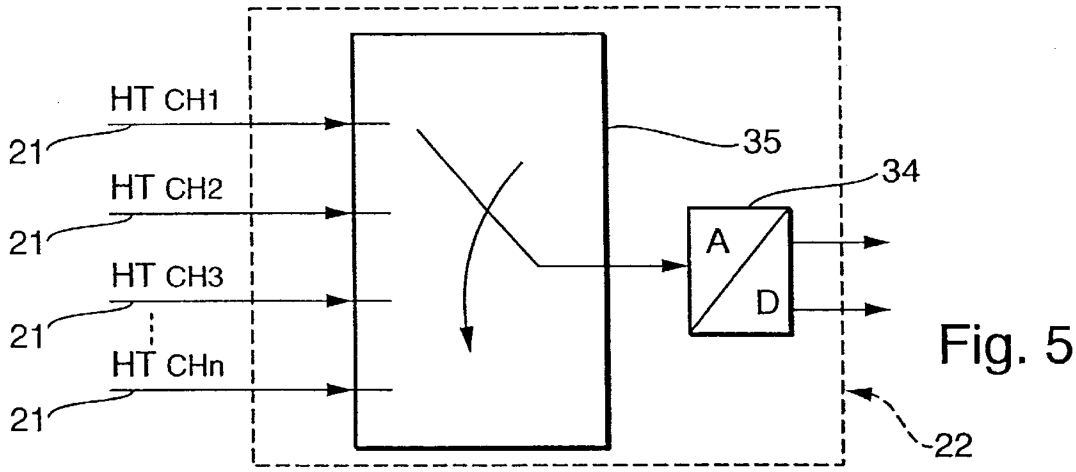
FIG. 5 shows a basic illustration of a second embodiment of a signal detection unit.
Figure 6:
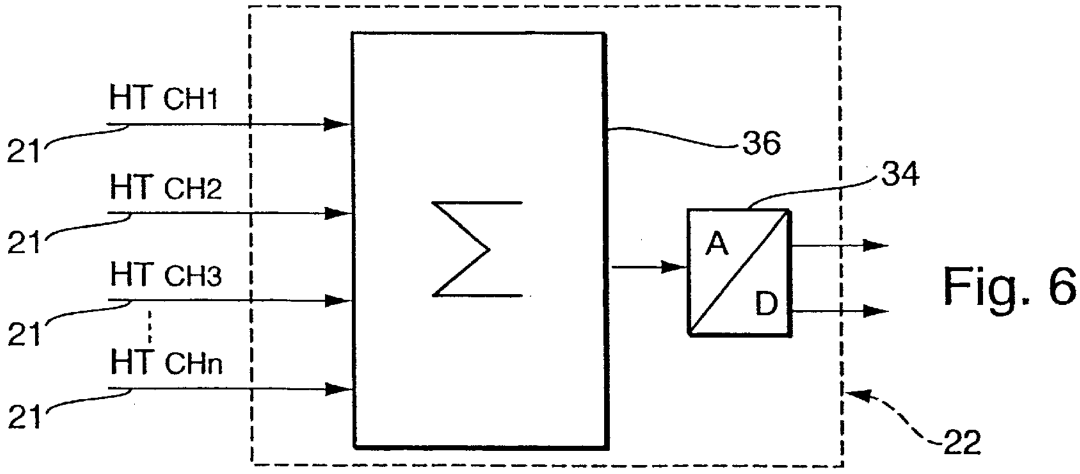
FIG. 6 shows a basic illustration of a third embodiment of a signal detection unit.

In accordance with FIGS. 4, 5 and 6, the signal detection unit 22 is preferably equipped with an analog/digital converter 34 in which the analog microphone signals, which have been produced by the tweeters operating as microphones and have been amplified by the microphone amplifiers, are converted into digital microphone signals suitable for digital processing. The analog microphone signals are supplied to the signal detection unit 22 via the signal lines 21. In this case, the signal detection unit 22 can, in principle, receive microphone signals from any number of microphones or tweeters operating as microphones. In FIGS. 4 to 6, the supplied, analog microphone signals are classified into “channels” denoted by “HT CH 1” to “HT CH n”.

In accordance with FIG. 4, the analog/digital converter 34 may be in the form of a multichannel converter which simultaneously digitizes a plurality of simultaneously incoming microphone signals and forwards them to the evaluation unit connected downstream.

As shown in FIG. 5, the analog/digital converter 34 may have an analog multiplexer 35 connected upstream which connects the individual incoming signal lines 21 to the input of the analog/digital converter 34 in cyclical succession.

In accordance with the embodiment shown in FIG. 6, the analog/digital converter 34 has an analog summation stage 36 connected upstream which adds all the incoming microphone signals and forms a sum signal therefrom. This sum signal is then supplied to the analog/digital converter 34 for digitization.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An audio system for a motor vehicle, comprising:

a loudspeaker installation for supplying sound to an audio chamber;

a control unit including a signal detection unit receiving microphone signals from at least one microphone exposed to said audio chamber and outputting said received microphone signals to an evaluation unit which extracted interference signals from said microphone signals, said control unit providing control signals as a function of said extracted interference signals in order to operate said loudspeaker installation;

said loudspeaker installation including at least one tweeter configured as said at least one microphone.

2. The audio system according to claim 1, wherein the tweeter is connected via a high-pass filter circuit to an output side of a loudspeaker amplifier wherein an input side of the loudspeaker amplifier receives the control signals from the control unit.

3. Audio system according to claim 2, wherein the tweeter is passively decoupled from the loudspeaker amplifier by means of a capacitor.

4. The audio system according to claim 2, wherein the tweeter is connected via a low-pass filter circuit to an input side of a microphone amplifier whose output side outputs the microphone signals to the signal detection unit.

5. The system according to claim 2, wherein said at least one tweeter is passively decoupled from a loudspeaker amplifier by a capacitor.

6. The system according to claim 2, wherein said control unit includes a signal detection unit receiving said microphone signals and including analog/digital converter for converting said microphone signals into digital microphone signals and outputting them to an evaluation unit.

7. The system according to claim 6, wherein said analog/digital converter is a multi channel converter simultaneously converting a plurality of simultaneously incoming microphone signals.

8. The system according to claim 6, wherein said signal detection unit includes an analog summation stage which adds a plurality of simultaneously incoming microphone signals and outputs said added signals to the analog/digital converter as a sum signal.

9. The audio system according to claim 1, wherein the signal detection unit includes an analog/digital converter which converts the microphone signals into digital microphone signals and outputs said digital signals to the evaluation unit.

10. The audio system according to claim 9, wherein the analog/digital converter is a multichannel converter which simultaneously converts a plurality of simultaneously incoming microphone signals.

11. The audio system according to claim 9, wherein the signal detection unit includes an analog multiplexer which supplies a plurality of simultaneously incoming microphone signals to the analog/digital converter in cyclical succession.

12. The audio system according to claim 9, wherein the signal detection unit includes an analog summation stage which adds a plurality of simultaneously incoming microphone signals and outputs said incoming signals to the analog/digital converter as a sum signal.

13. The audio system to claim 1, wherein the control unit controls and/or regulates at least one of the following functions on the basis of the interference signals: equalizing, compression, limiter, level matching, filter matching.

14. A motor vehicle audio system including a loudspeaker installation and a control unit, said loudspeaker installation including at least one tweeter configured as a microphone for a first frequency range and as a loudspeaker tweeter for a second frequency range wherein first frequency range is less than said second frequency range and wherein the control unit includes a means for receiving microphone signals from said tweeter and a means for extracting interference signals from said microphone signals to provide control signals as a function of said interference signals in order to operate said loudspeaker installation.

15. System according to claim 14 further including a loudspeaker amplifier having an input side receiving the control signals from the control unit and an output side connected to one of said at least one tweeter through a high pass-filter circuit.

* * * * *